(12) United States Patent
Shi et al.

(10) Patent No.: US 7,964,741 B2
(45) Date of Patent: Jun. 21, 2011

(54) BIBENZOTHIOPHENE DERIVATIVES

(75) Inventors: Jianmin Shi, Rockville, MD (US); Eric W. Forsythe, Silver Spring, MD (US); David C. Morton, Columbia, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 481 days.

(21) Appl. No.: 12/123,648

(22) Filed: May 20, 2008

(65) Prior Publication Data

US 2009/0292130 A1 Nov. 26, 2009

(51) Int. Cl.
*C07D 333/74* (2006.01)
(52) U.S. Cl. .......................................... 549/41
(58) Field of Classification Search ........................ 549/41
See application file for complete search history.

(56) References Cited

U.S. PATENT DOCUMENTS

| | | | |
|---|---|---|---|
| 6,645,401 B2 | 11/2003 | Giles et al. | |
| 6,695,978 B2 | 2/2004 | Worrall et al. | |
| 6,806,374 B2 | 10/2004 | Heeney et al. | |
| 6,841,677 B2 | 1/2005 | Heeney et al. | |
| 6,913,710 B2 | 7/2005 | Farrand et al. | |

FOREIGN PATENT DOCUMENTS

JP 2008140989 6/2008

OTHER PUBLICATIONS

Applied Physics Letter, 90, 012112, 2007.
J. Org. Chem. vol. 44, p. 2491-2493, (1979).

*Primary Examiner* — Taofiq Solola
(74) *Attorney, Agent, or Firm* — Avrom David Spevack

(57) ABSTRACT

Compounds containing bibenzochalcogenophene structures are provided in which the chalcogenide is sulfur, selenium, or tellurium. The compounds are characterized by planarity, rigid conjugation structure and high charge mobility making them useful as organic semiconductor in optical devices, electronic devices and integrated devices like organic field effect transistors (OFET) for thin film transistor liquid crystal display (LCD), electrophoretic display such as electronic paper, organic light emitting diode (OLED) for flat panel displays, organic radio frequency identification (ORFID) tags, organic photovoltaic (OPV), sensor devices, and analog and digital electronics.

17 Claims, No Drawings

BIBENZOTHIOPHENE DERIVATIVES

GOVERNMENT INTEREST

The invention described herein may be manufactured, used, and licensed by or for the United States Government.

FIELD OF THE INVENTION

This invention in general relates to bibenzochalcogenophene derivatives, and more specifically to 3,4:3',4'-bibenzo[b]thiophene derivatives.

BACKGROUND OF THE INVENTION

The electronic conductivity of organic materials lies between that of metals and insulators, spanning a broad range of $10^{-9}$ to $10^3/\Omega$-cm. The interest in this field can be traced back to early 1900s when the photoconduction of solid anthracene was discovered. A considerable amount of research was devoted to understand the charge transport properties of organic semiconductors starting 1950s and to potential use of organic semiconductors in electronic devices began in late 1980s.

The interest in the study of organic semiconductors in particular sparks from the fact that these organic electronic devices are easier to fabricate than traditional silicon based semiconductors that require rigorous processing techniques and high temperatures. Also organic semiconductors can be designed by computer assist modeling to improve their charge transport properties in electronic field to fit a variety of application requirements or by incorporation of functional groups in the molecules and improving their physical properties to make low temperature vapor deposition process possible, or by improving solubility in solvents that led to form semiconductor thin film by cost-effective solution deposition process.

Many organic materials have been studied as organic semiconductors. Among them arylamines were widely studied as organic photoconductors (OP) in early 1970s and later as an efficient hole transport materials for OLED devices. Fused aryl hydrocarbon molecule, more typically pentacene and its derivatives have shown the high charge mobility both processed by vapor deposition and solution coating deposition process.

The most known regular poly(3-hexylthiophene) has been studied and reported with low charge mobility and low current on/off ratio. Most recently polythionphene were studied as organic thin film transistors (OTFT) with a research focus on improving the charge mobility, easy to synthesize, good processability and oxidative stability. These improvements can be achieved by designing the new monomers, oligomers, and polythiophene molecules with good planarity and conjugation [Applied Physics Letter, 90, 012112, 2007 and references therein]. A few of thiophene containing examples have been disclosed in U.S. Pat. Nos. 6,695,978; 6,645,401; 6,806,374; 6,841,677; 6,913,710 and were shown as follows:

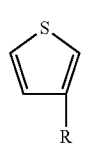
Thiophene

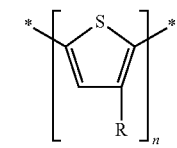
Polymer with thiophene moiety

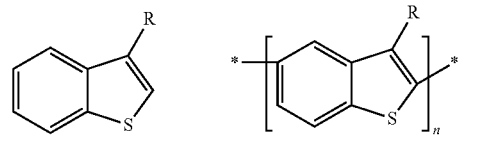
Benzo[b]thiophene    Polymer with benzo[b]thiophene moiety

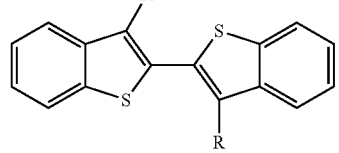
2, 2'-bisbenzo[b]thiophene

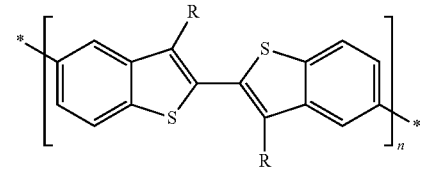
Polymer with 2, 2'-bisbenzo[b]thiophene moiety

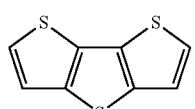
Dithienothiophene (DTT)
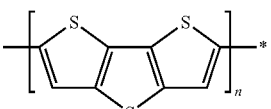
Polymer with DTT moiety

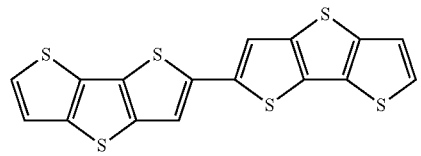
α, α'-Bis (dithieno[3,2-b:2',3'-d]thiophene (BDT)

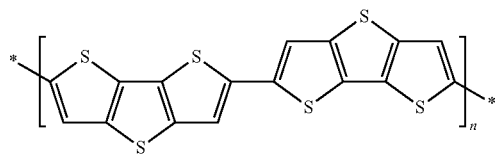
Polymer with BDT moiety

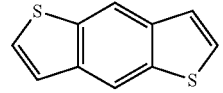
Benzo [1,2-b:4,5-b'] dithiophene

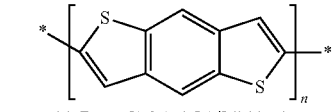
Polymer with Benzo[1,2-b:4,5-b']dithiophene moiety

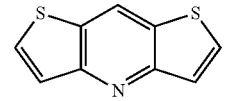
Dithieno[3,2-b:2',3'-e]pyridine (DTP)

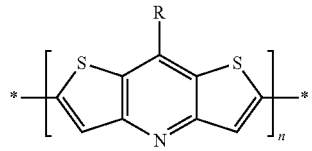
Polymer with DTP moiety

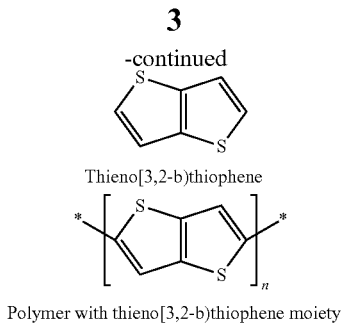

Thieno[3,2-b]thiophene

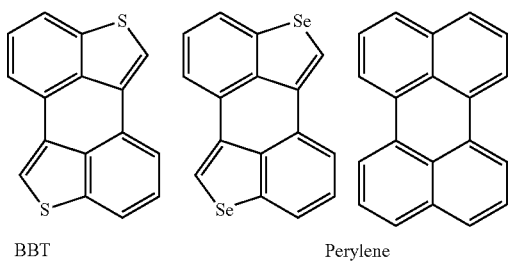

Polymer with thieno[3,2-b]thiophene moiety 3,4:3',4'-bibenzo[b]thiophene (BBT) which has an isoelectronic structure with perylene which has been known as one of most stable organic materials. BBT has been reported and its iodine complex with very similar properties to the perylene-iodine solids, including its electrical conductivity [J. Org. Chem. Vol. 44, page 2491-2493, (1979)].

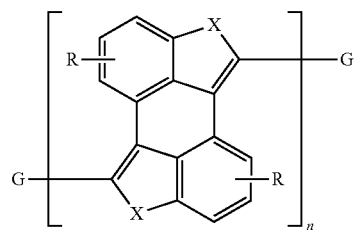

BBT  Perylene

The bibenzochalcogenophenes containing S, bibenzothiophene, Se, bibenzoselenophene or Te bibenzotellurophene and its selenium analogs have a great planarity and rigid conjugation ring system. These structure features are important in improving charge mobility and stability toward environmental oxygen exposure.

Thus, there exists a need for new compounds containing a bibenzothiophene structure that provides the planarity, rigid conjugation system and charge mobility of this structure. There exists a further need for new compounds containing bibenzothiophene structures that are easily synthesized, and are readily processed either by vapor deposition to from uniform thin film or by cost-effective solution coating deposition process with good environmental oxygen exposure stability.

SUMMARY OF THE INVENTION

A bibenzochalcogenophene compound of sulfur, selenium, or tellurium is provided. The compound is particularly well suited for use as an organic semiconductor. The compound has having the formula:

where
X is S, Se or Te;
R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom;

G in each occurrence is independently fluorine, chlorine, bromine, iodine, cyano, isocyano, R, with the proviso that R is not H, Q, E or

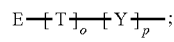

E is K or Q with the proviso R is not H;
T is independently in each occurrence of each of T is -M-(P—$R_3^1$)$_q$(R)$_{3-q}$, or R-Q with the proviso that R is not H;
Y is independently in each occurrence of each of Y is -M-(P—$R_3^1$)$_q$(R)$_{3-q}$, or R-Q with the proviso that R is not H;
Q is a polymerizing functional group of

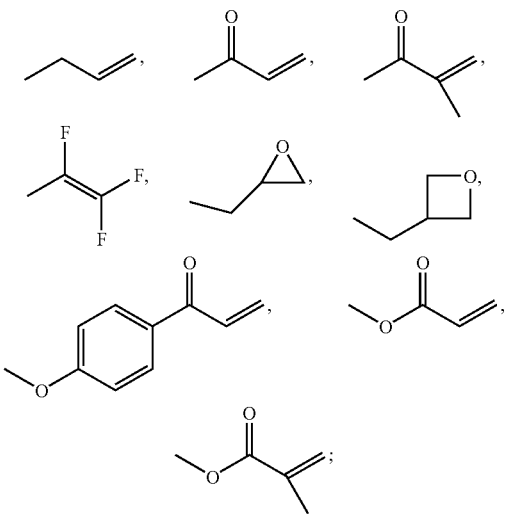

o is an integer from 0 to 100 inclusive;
p is an integer from 0 to 100 inclusive;
M is a transition metal of Pt, Ni or Pd;
$R^1$ is independently in each occurrence $C_1$-$C_{12}$ alkyl;
q is an integer from 0 to 3 inclusive; and
n is an integer from 1 to 250 inclusive.

DESCRIPTION OF THE PREFERRED EMBODIMENTS

A compound of the present invention has utility as an organic semiconductor in optical electronic devices, more typically used as organic field effect transistors (OFET) in integrated electronic devices, such as liquid crystal display (LCD), electronic paper, organic light emitting diode (OLED) display panel, organic radio frequency identification (ORFID) tags, organic photovoltaic (OPV), sensor devices, and analog and digital electronics.

The present invention a compound containing bibenzochalcogenophene structure of formula I provide several attributes that are well suited for use as high charge mobility organic semiconductors in organic optical and electronic devices. The chalcogenides of sulfur, selenium, and tellurium are operative herein as bibenzochalcogenophenes. The compound of formula I has the structure

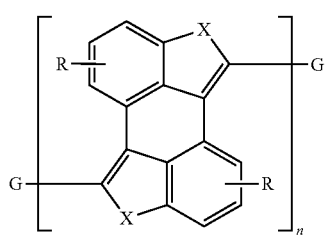

I where
X is S, Se or Te;
R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom;
G in each occurrence is independently fluorine, chlorine, bromine, iodine, cyano, isocyano, R with the proviso R is not H, Q, E or

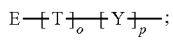

E is R or Q with the proviso R is not H;
T is independently in each occurrence of each of T is -M-(P—$R_3^1$)$_q$(R)$_{3-q}$, or R-Q with the proviso that R is not H;
Y is independently in each occurrence of each of Y is -M-(P—$R_3^1$)$_q$(R)$_{3-q}$, or R-Q with the proviso that R is not H;
Q is a polymerizing functional group of

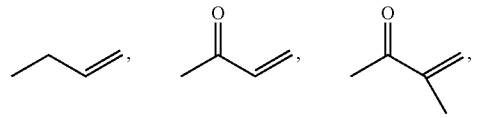

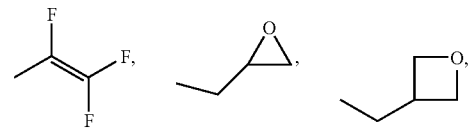

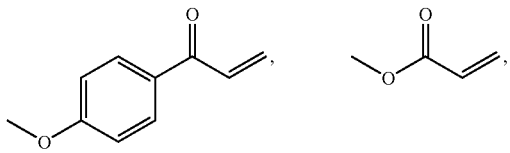

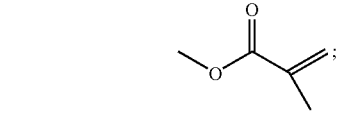

o is an integer from 0 to 100 inclusive;
p is an integer from 0 to 100 inclusive;
M is a transition metal of Pt, Ni or Pd;
$R^1$ is independently in each occurrence $C_1$-$C_{12}$ alkyl;
q is an integer from 0 to 3 inclusive; and
n is an integer from 1 to 250 inclusive.
An inventive compound is operative as a high charge mobility small molecular organic semiconductor that is optionally fabricated by vacuum vapor deposition to form high uniform thin film in organic electronic devices. The following especially preferred examples are listed, but not limited, are typical useful for achieving above advantages as an organic semiconductors in optical and electronic devices.

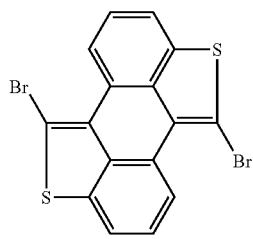

I-01

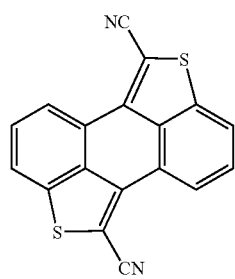

I-02

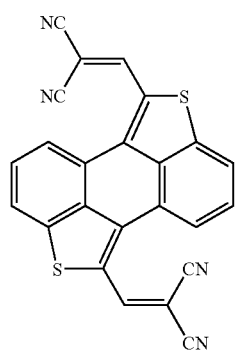

I-06

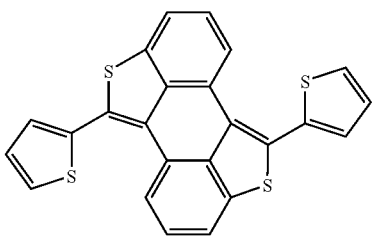

I-04

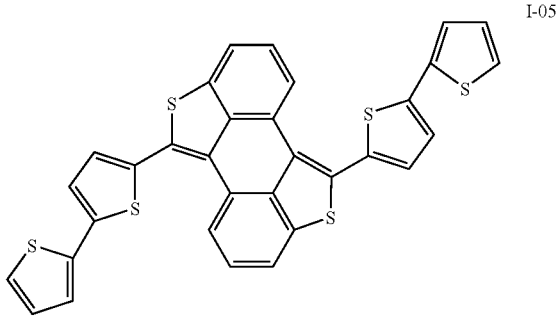

I-05

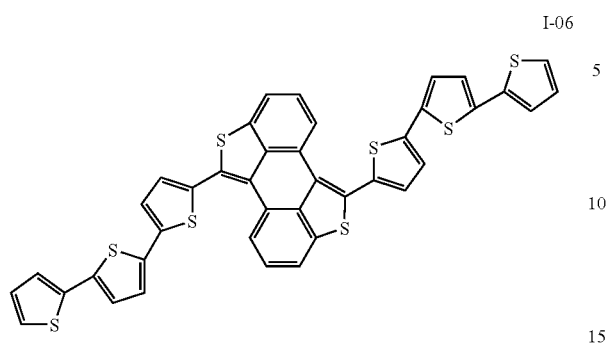
I-06
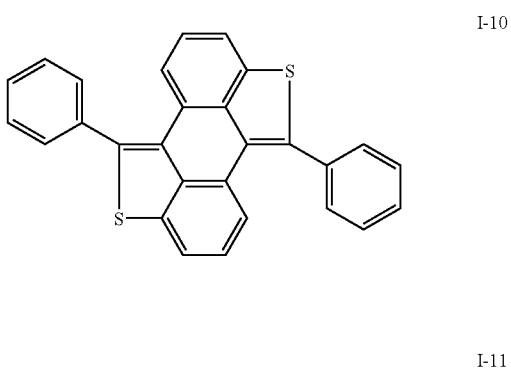
I-10
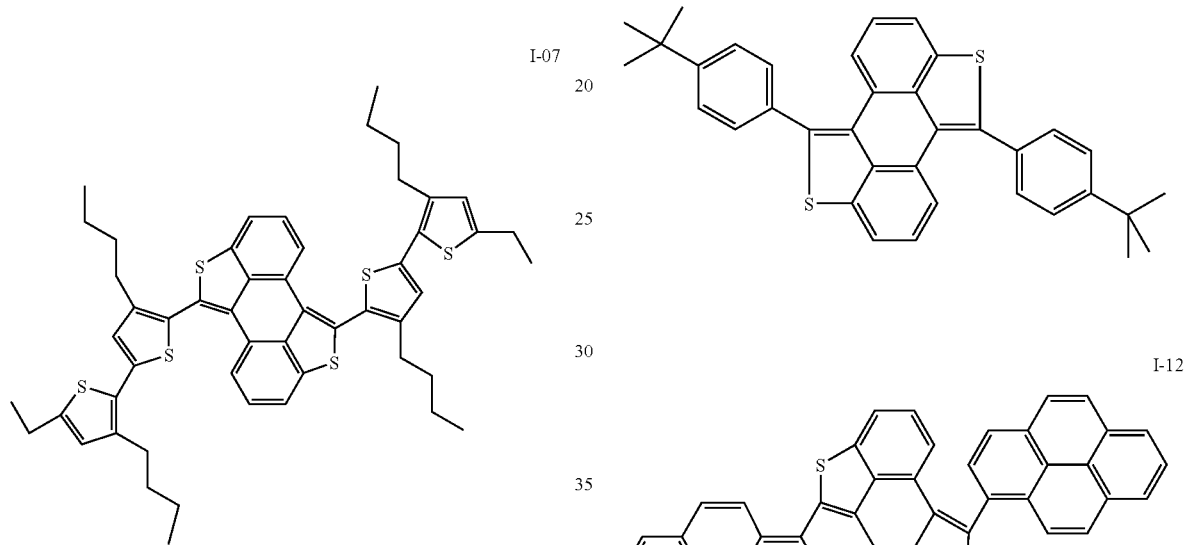
I-07
I-11
I-12
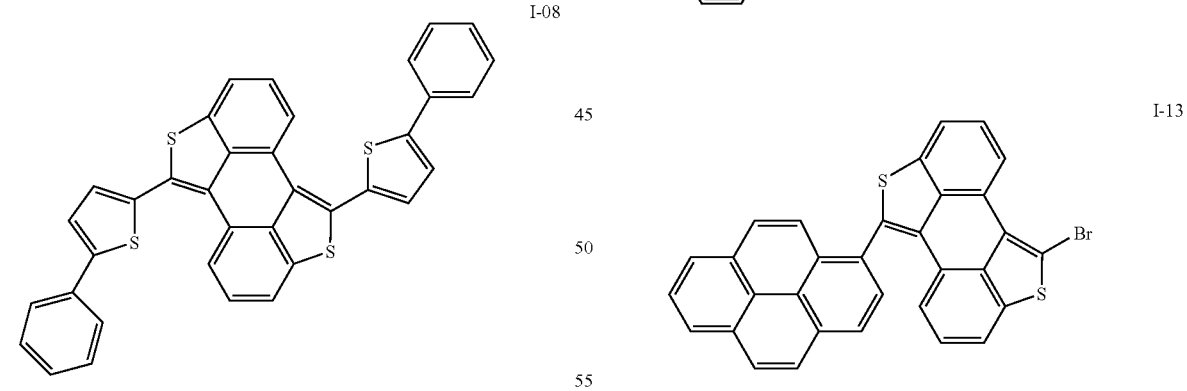
I-08
I-13
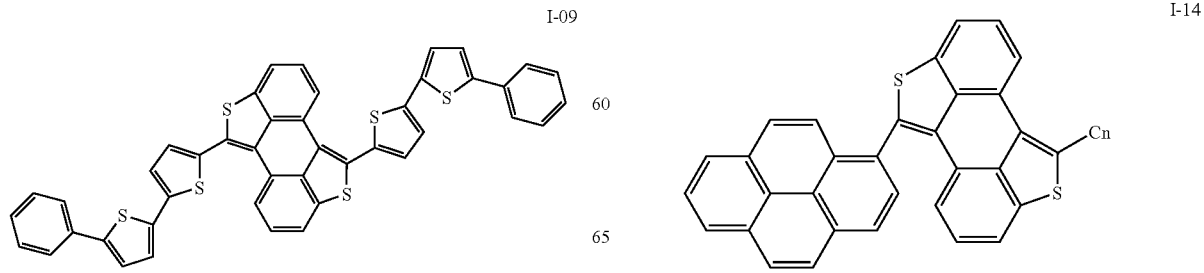
I-09
I-14

I-15

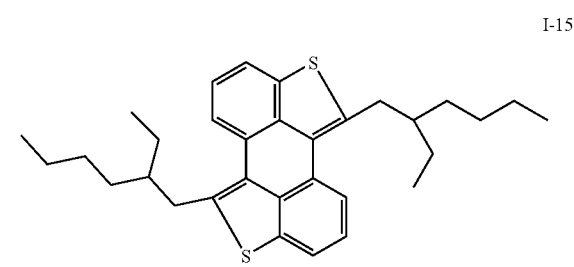

I-16

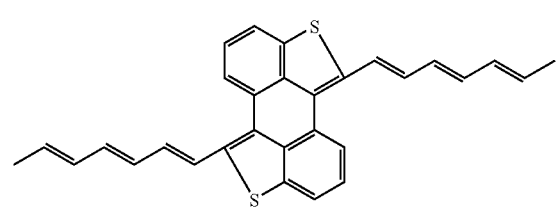

I-17

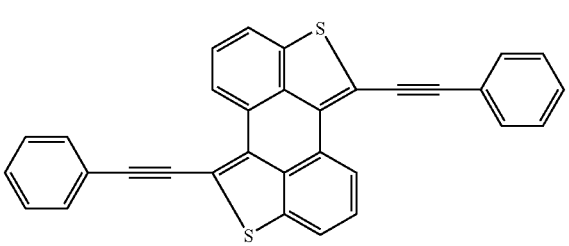

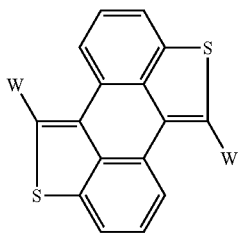

| I-018 | W = F |
| I-019 | W = Cl |
| I-20 | W = I |

I-21

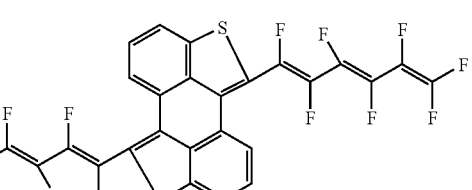

An inventive compound is also operative as a high charge mobility small molecular organic semiconductor that is optionally fabricated by cost-effective solution coating process to form high uniform thin film in organic electronic devices. The following especially preferred examples are listed, but not limited, are typical useful for achieving above advantages as an organic semiconductors in optical and electronic devices.

II-01

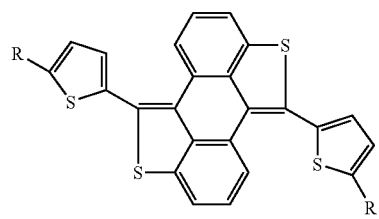

II-02

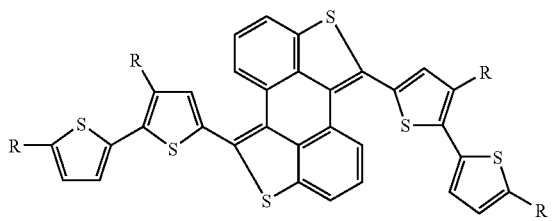

II-03

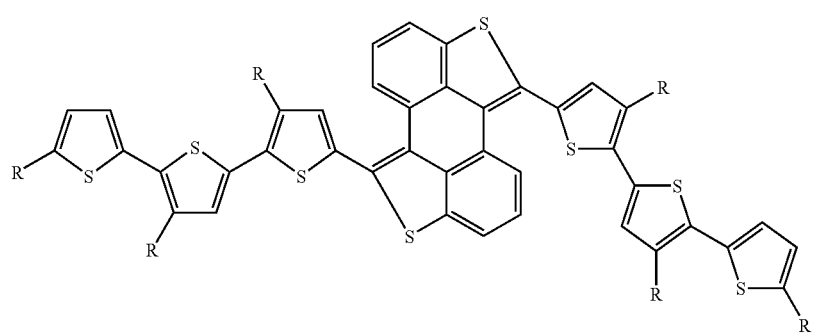

where R is in each occurrence of II-02 and II-03 independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom.

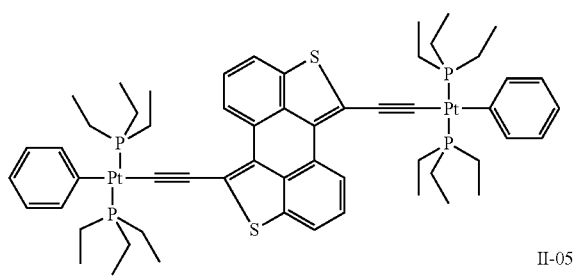

II-04

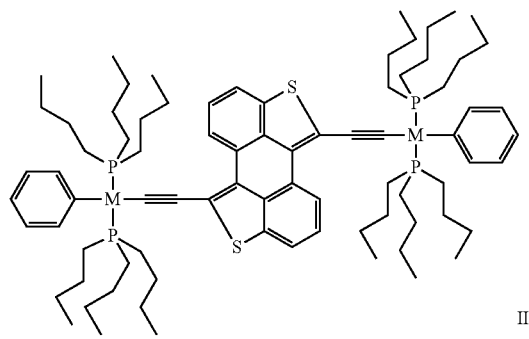

II-05

II-06 where R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom. Preferably, R bonded to M in each occurrence is $C_4$-$C_{48}$ perfluoroaryl, $C_4$-$C_{48}$ aryl, $C_4$-$C_{48}$ heteroatom containing aryl the heteroatom being O, N, S or Se, $C_4$-$C_{48}$ heteroatom containing perfluoroaryl, and M is a transition metal of Pt, Ni, and Pd. Pt is a preferred atom for M.

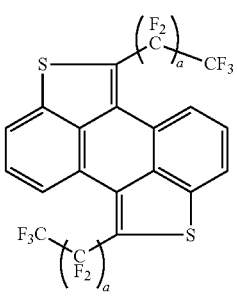

II-07 where a is integer from 4 to 48 carbon atoms.

An inventive compound is also operative as a high charge mobility polymeric organic semiconductor that is optionally fabricated by cost-effective solution coating process to form high uniform thin film in organic electronic devices. The following especially preferred examples are listed, but not limited, are typical useful for achieving above advantages as an organic semiconductors in optical and electronic devices.

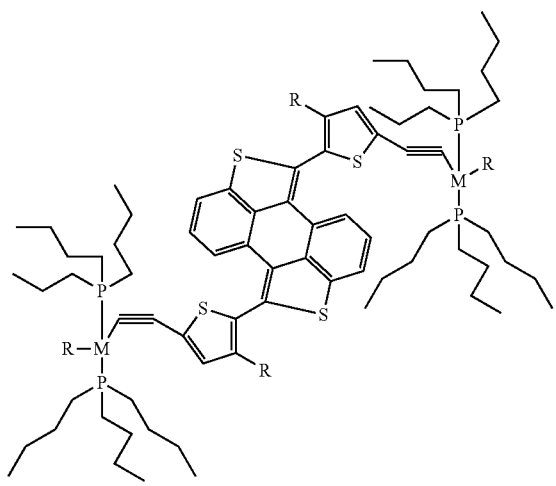

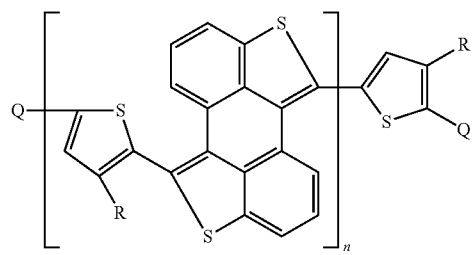

III-01

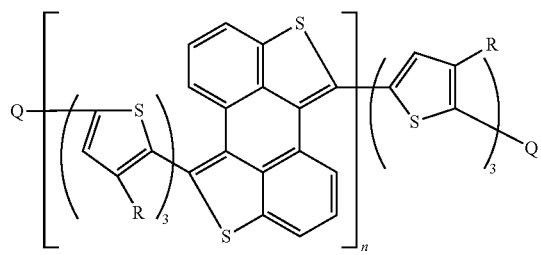

III-02

-continued
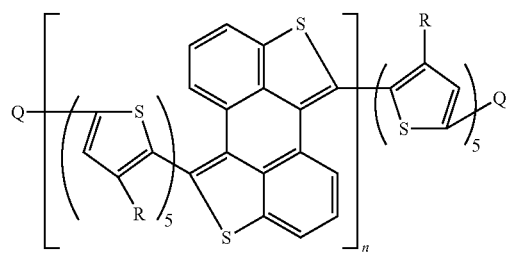
III-03
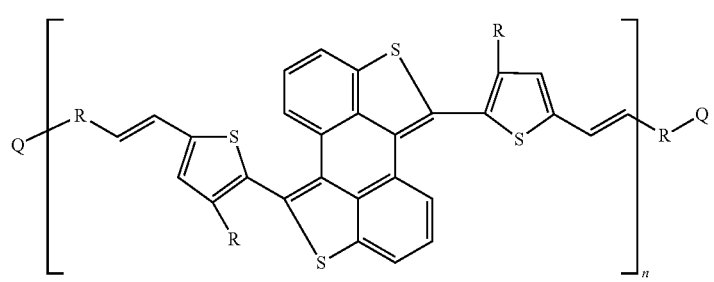
III-04
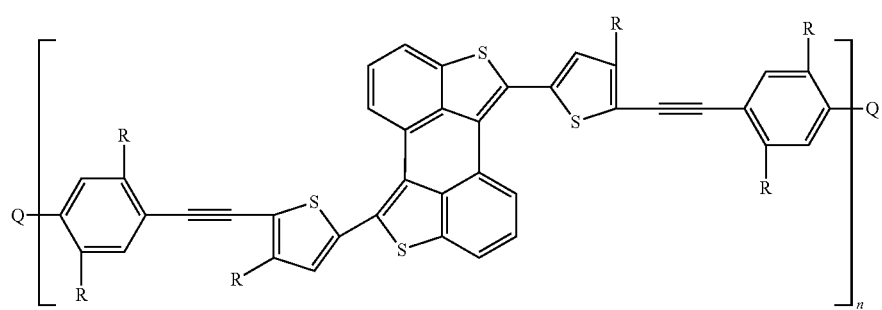
III-05
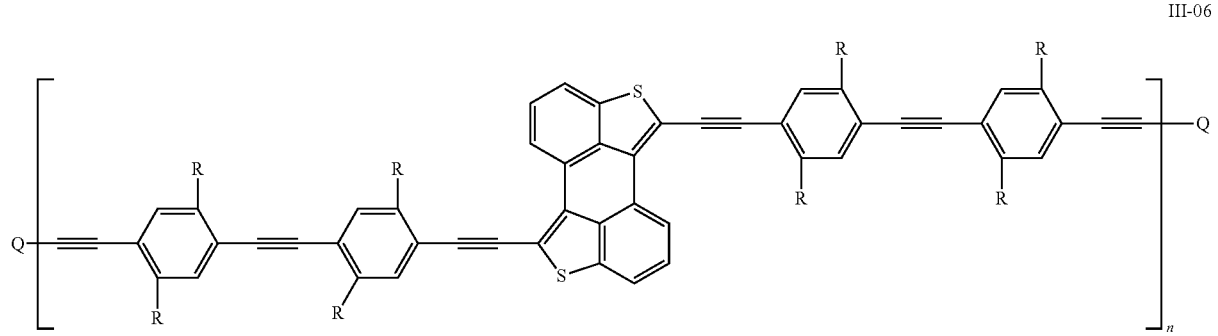
III-06
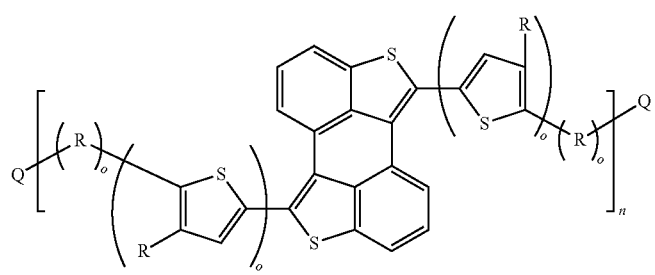
III-07

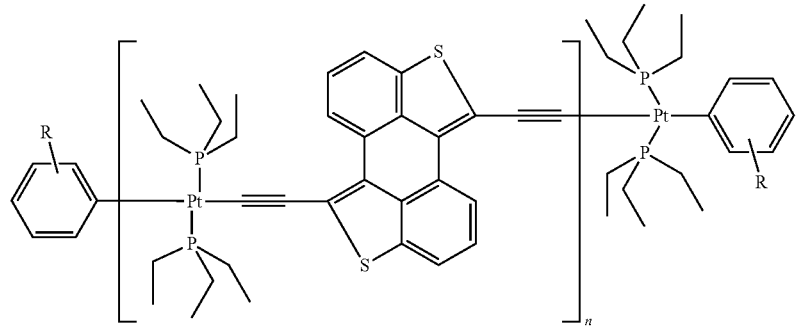

III-08

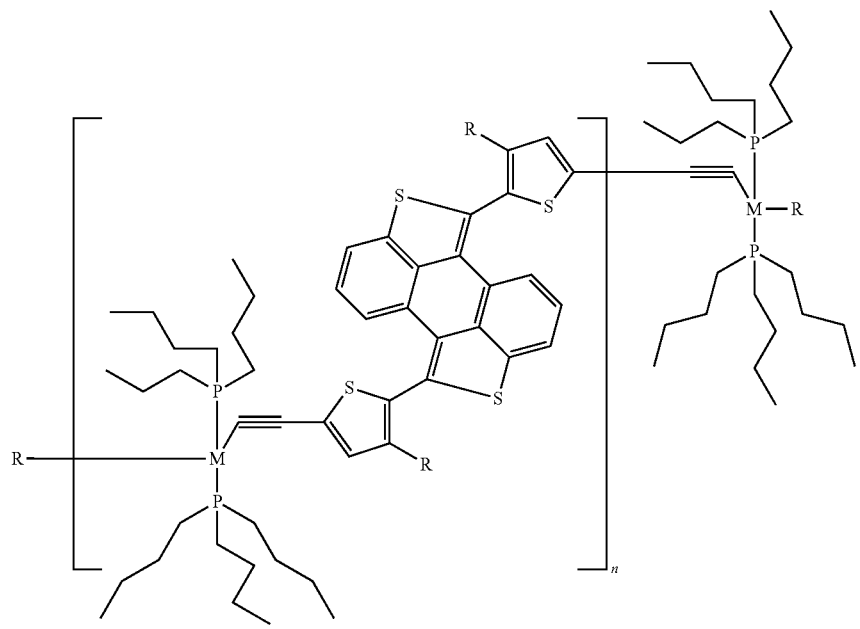

III-10 where with respect to formulae III-01-10

R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom. Preferably, R bonded to M in each occurrence is $C_4$-$C_{48}$ perfluoroaryl, $C_4$-$C_{48}$ aryl, $C_4$-$C_{48}$ heteroatom containing aryl the heteroatom being O, N, S or Se, $C_4$-$C_{48}$ heteroatom containing perfluoroaryl, and M is a transition metal of Pt, Ni, or Pd. Pt is a preferred atom for M; o is in each occurrence independently an integer from 1 to 100.

E is R or Q. Q is a functional group which is able to initiate polymerization process to form polymer, or with other monomers to form copolymer or random polymers. Q is preferably selected from, but not limited, following:

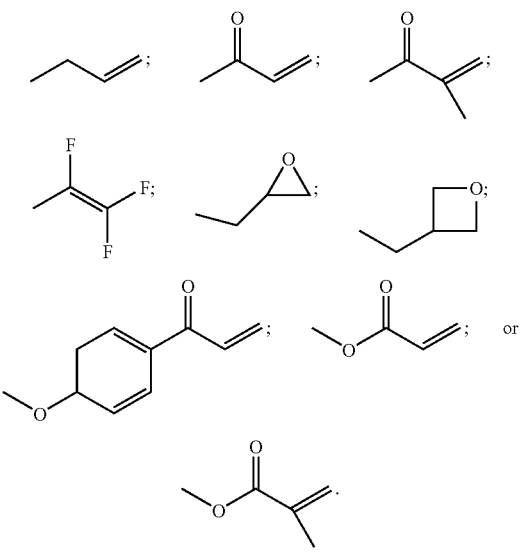

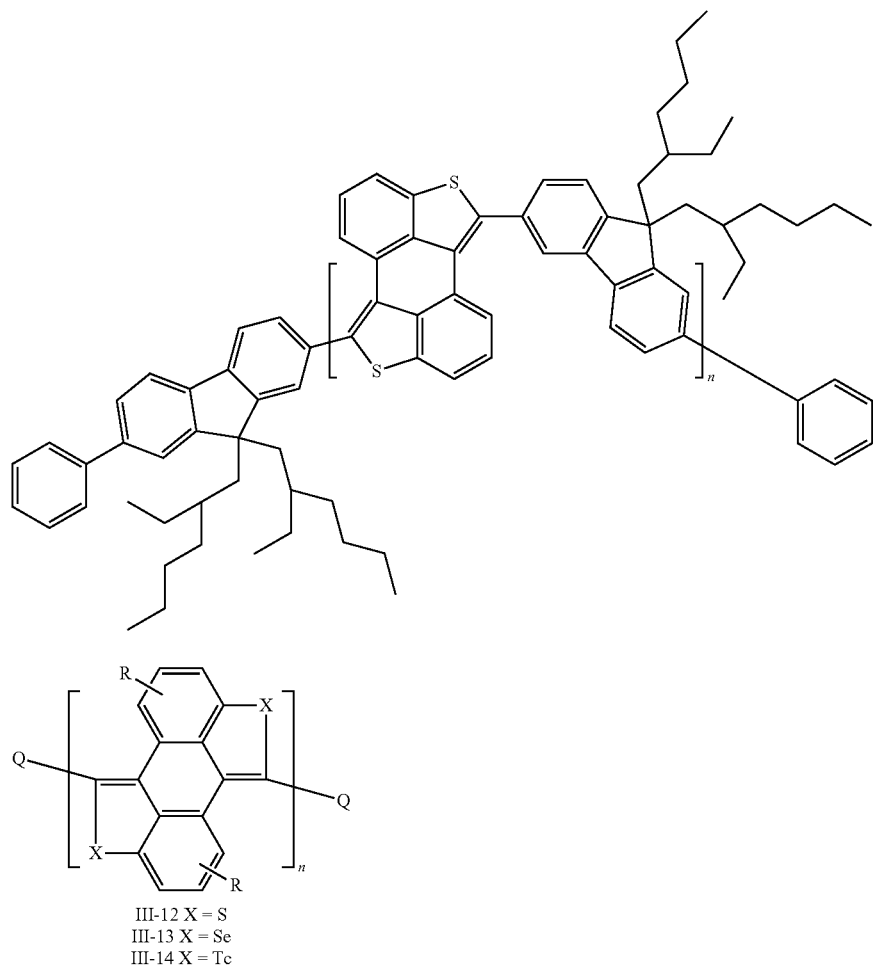

III-11

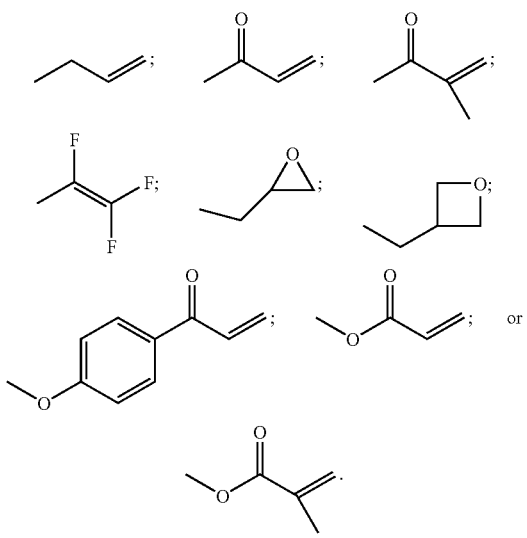

III-12 X = S
III-13 X = Se
III-14 X = Te where with respect to formulae III-11-14

R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom. Preferably, R bonded to M in each occurrence is $C_4$-$C_{48}$ perfluoroaryl, $C_4$-$C_{48}$ aryl, $C_4$-$C_{48}$ heteroatom containing aryl the heteroatom being O, N, S or Se, $C_4$-$C_{48}$ heteroatom containing perfluoroaryl, and M is a transition metal of Pt, Ni, or Pd. Pt is a preferred atom for M.

o is in each occurrence independently an integer from 1 to 100.

E is R or Q. Q is a functional group which is able to initiate polymerization process to form polymer, or with other monomers to form co-polymer or random polymers. Q is preferably selected from, but not limited, following:

n is integer from 1 to 250 inclusive.

The following described detail synthetic schemes particular reference to certain preferred embodiments thereof, but it will be understood that variations and modifications can be effected within the spirit and scope of the invention.

An inventive compound is readily synthesized through the intermediate, 2,7-dibromo-3,4:3',4'-bibenzo[b]thiophene (I-01), 2,7-dibromo-3,4:3',4'bibenzo[b]selenophene, or 2,7-dibromo-3,4:3',4'-bibenzo[b]tellurophene according to the following illustrated schemes or similar approaches.

Scheme 1:

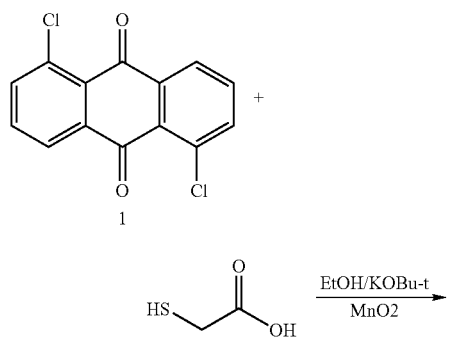

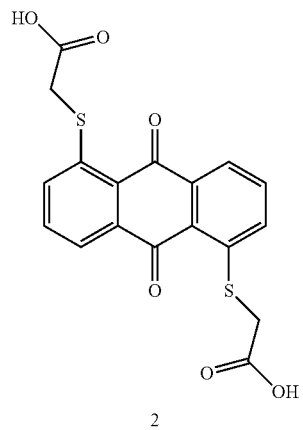

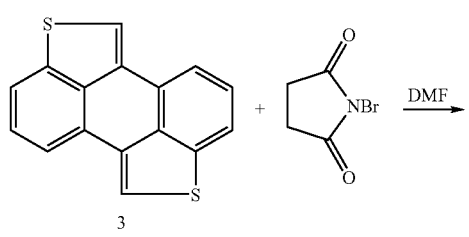

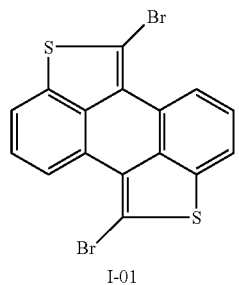

Scheme 2:

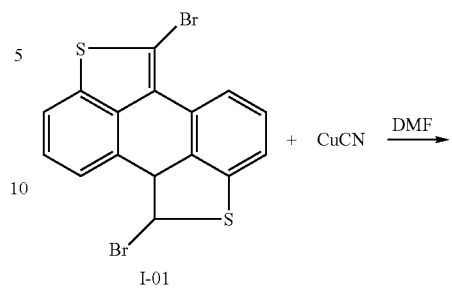

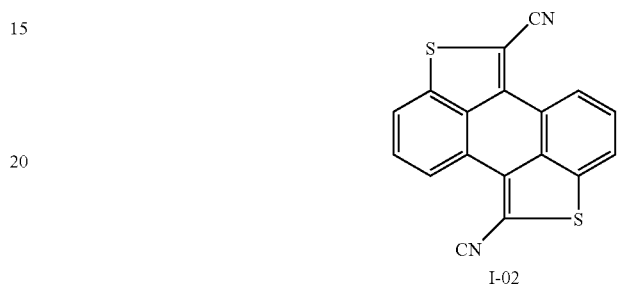

Scheme 3:

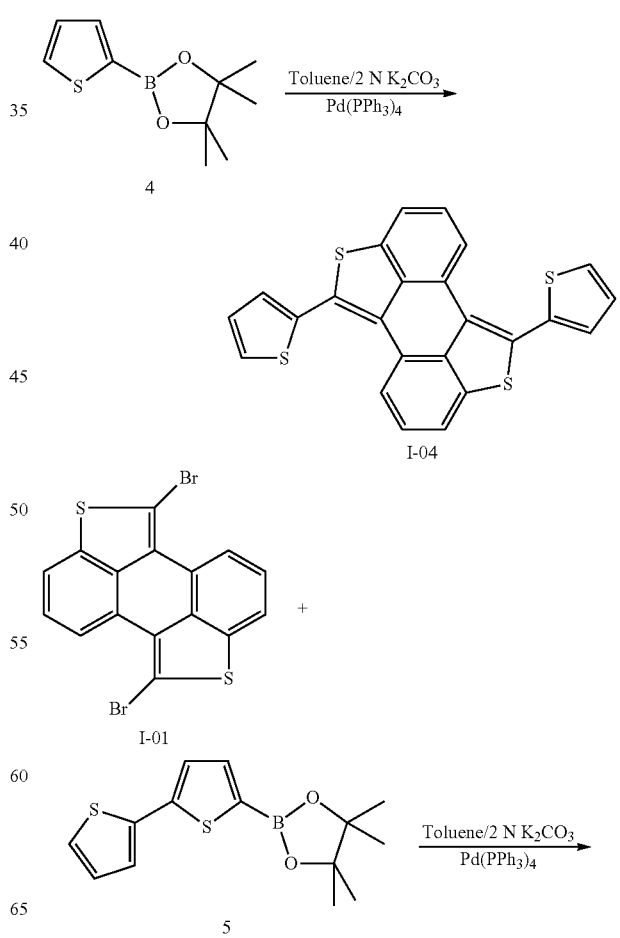

where Et is ethyl, KOBu-t is potassium tert-butoxide, Ac$_2$O is acetone and DMF is dimethylformaldehyde.

-continued
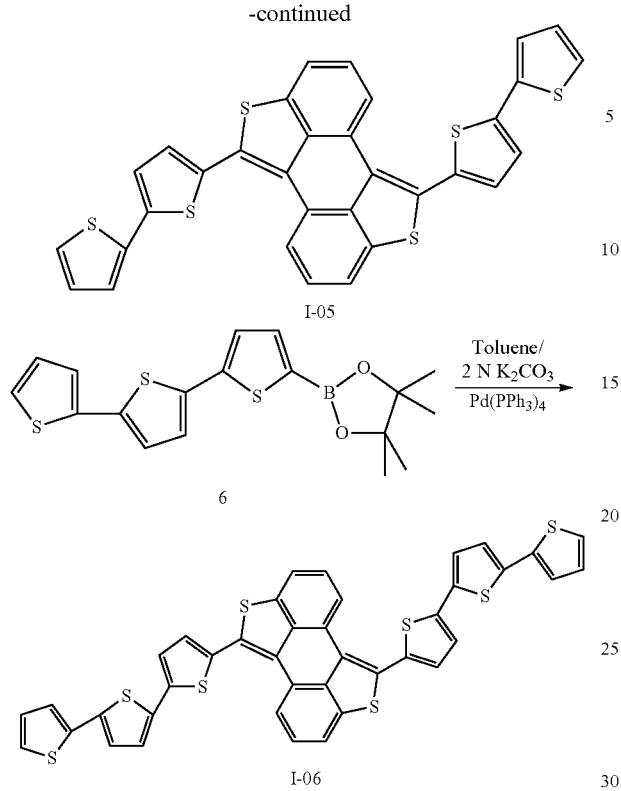
where Ph is phenyl
Scheme 4:
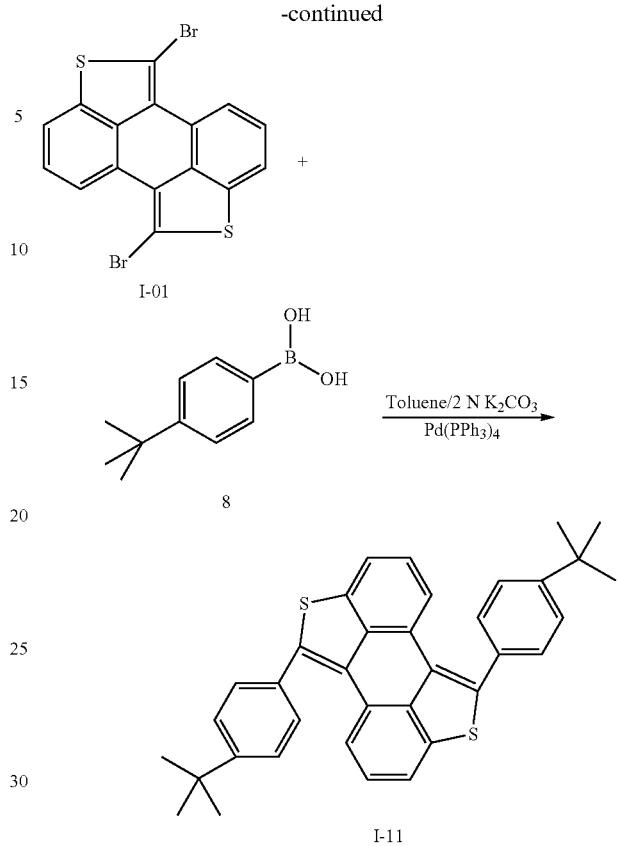
Scheme 5:
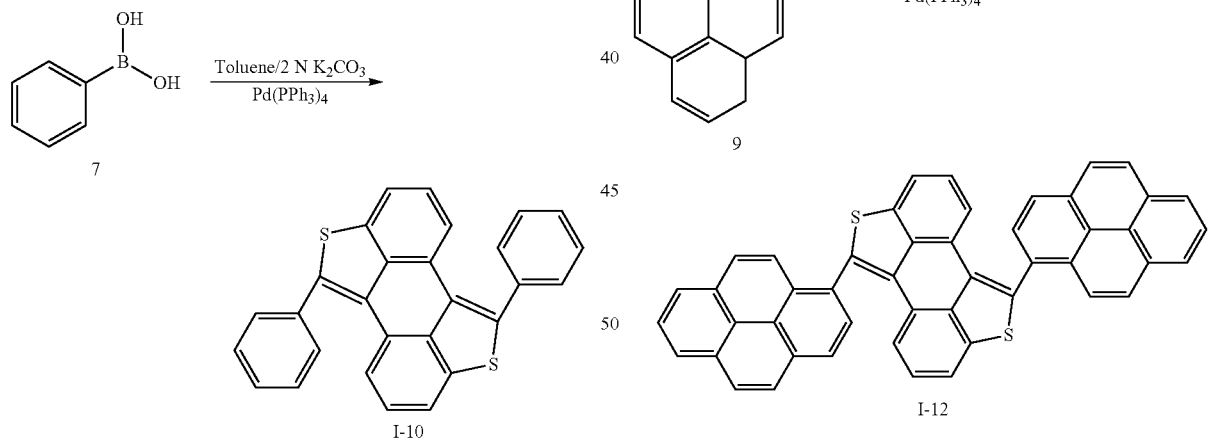
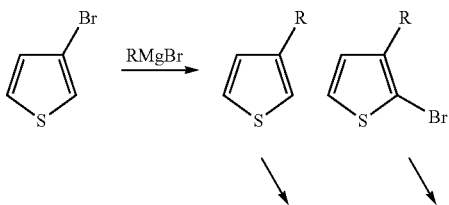

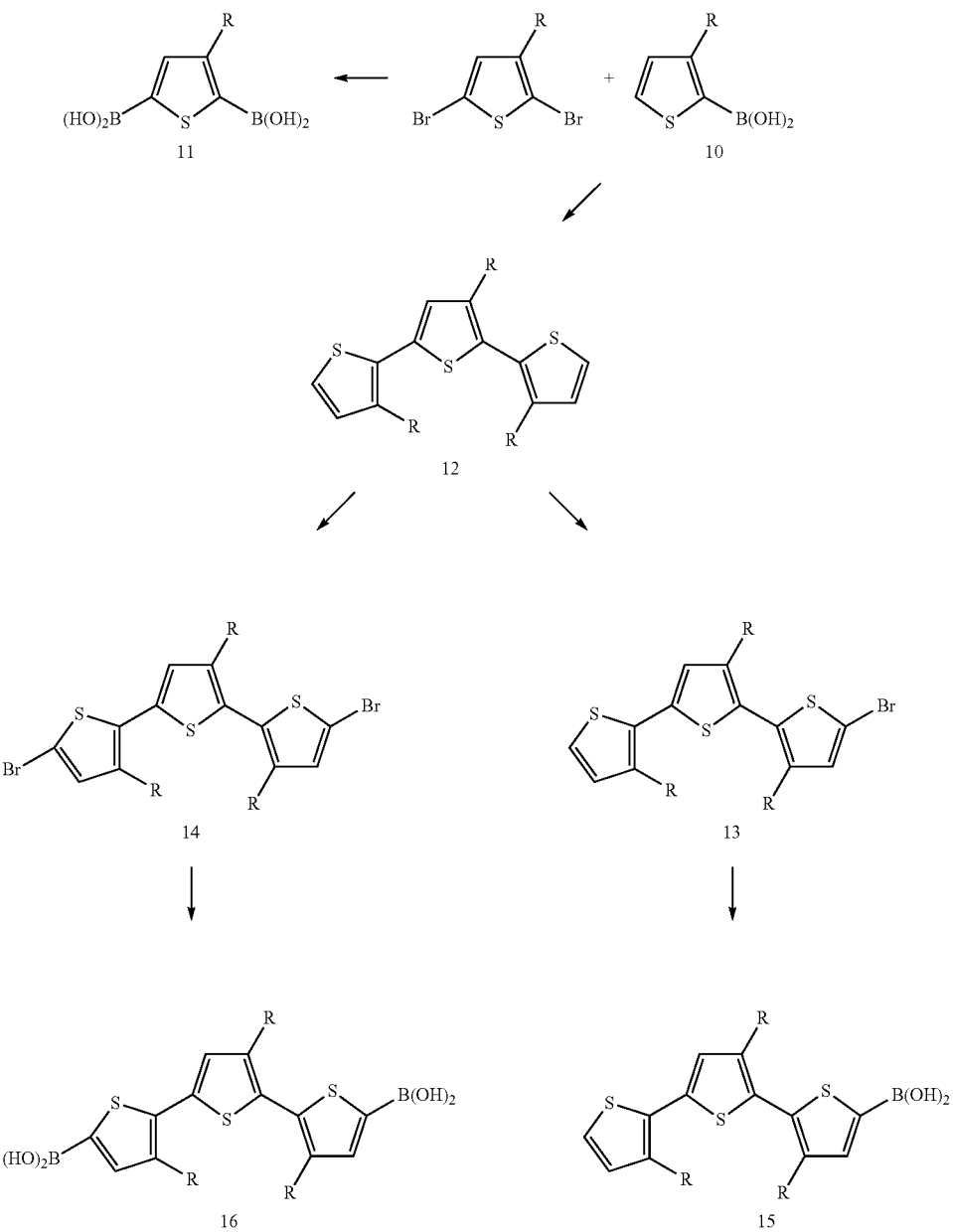
Scheme 6:
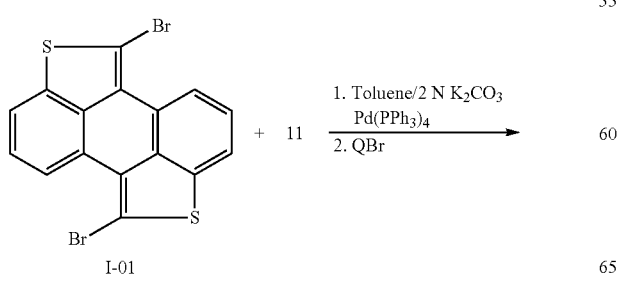
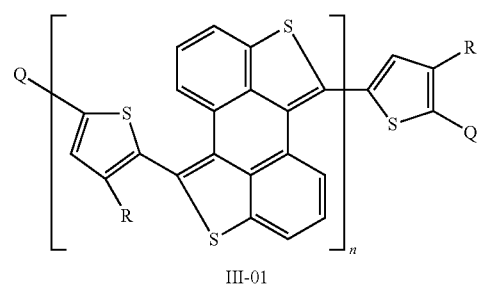

Scheme 7:
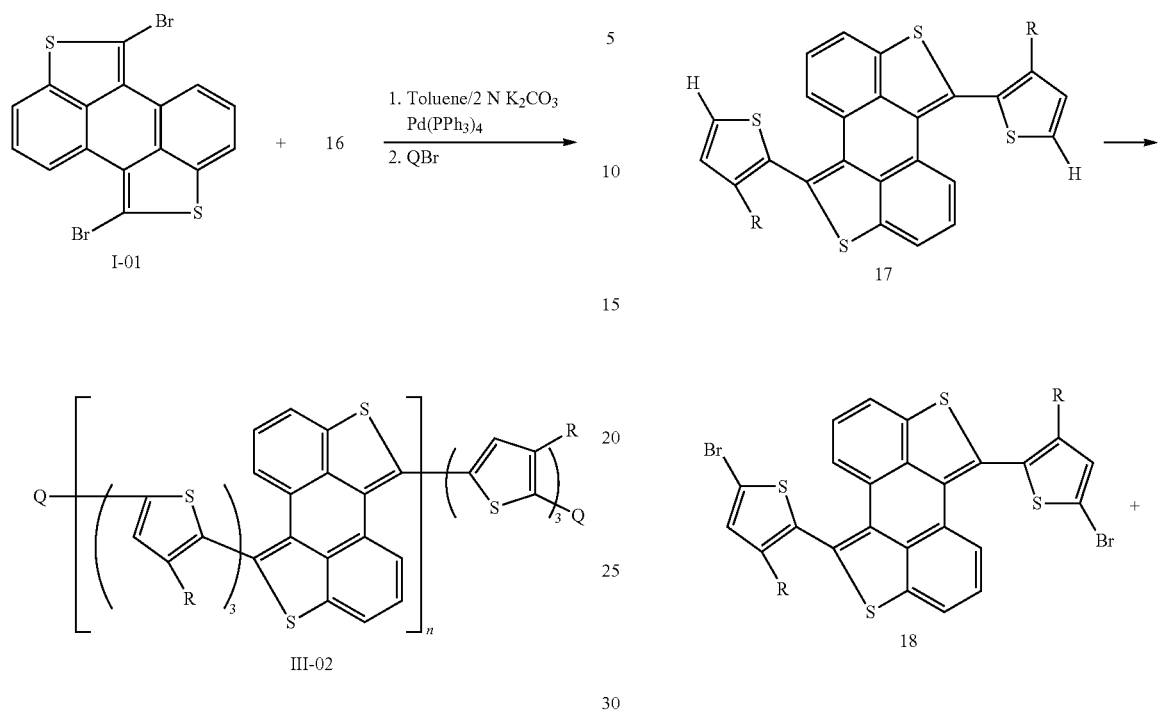
Scheme 8:
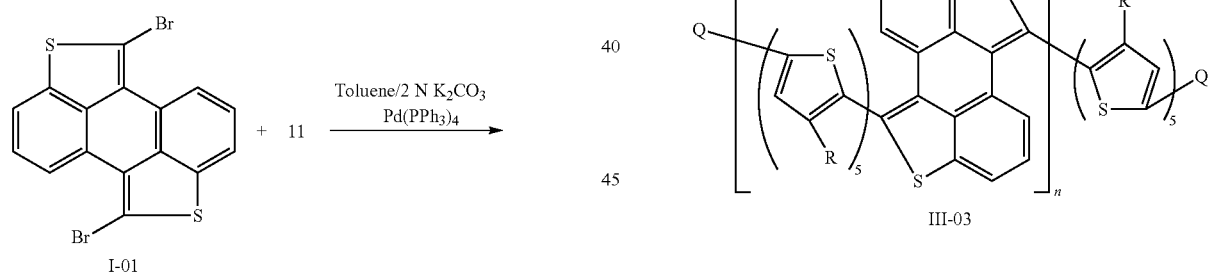
Scheme 9:
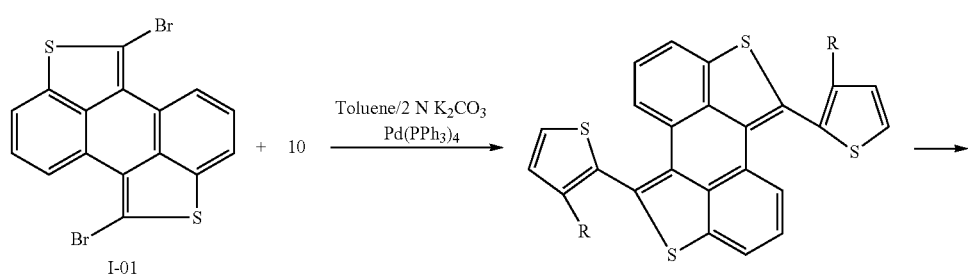

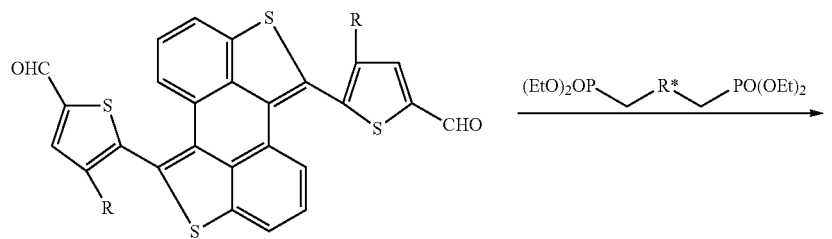
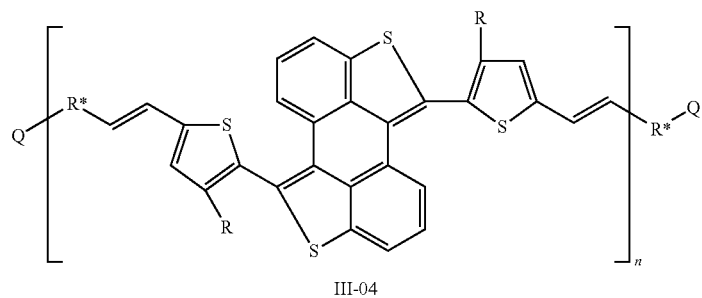
where R* is in each occurrence independently $C_4$-$C_{48}$ aryl, $C_4$-$C_{48}$ aryl containing a heteroatom of O, S, N, Se, or Te, $C_4$-$C_{48}$ fluoro aryl, $C_4$-$C_{48}$ fluoro aryl containing the heteroatom, $C_4$-$C_{48}$ perfluoro aryl, or $C_4$-$C_{48}$ perfluoro aryl containing the heteroatom.
Scheme 10:
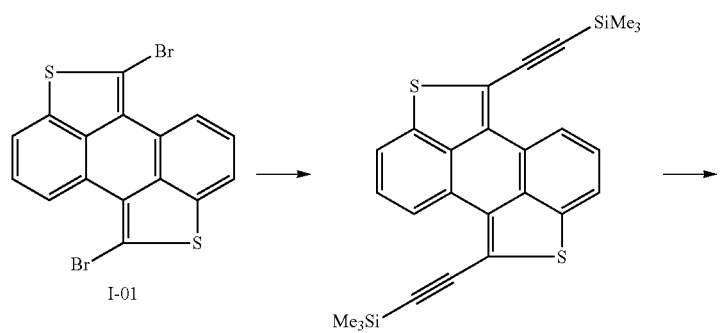

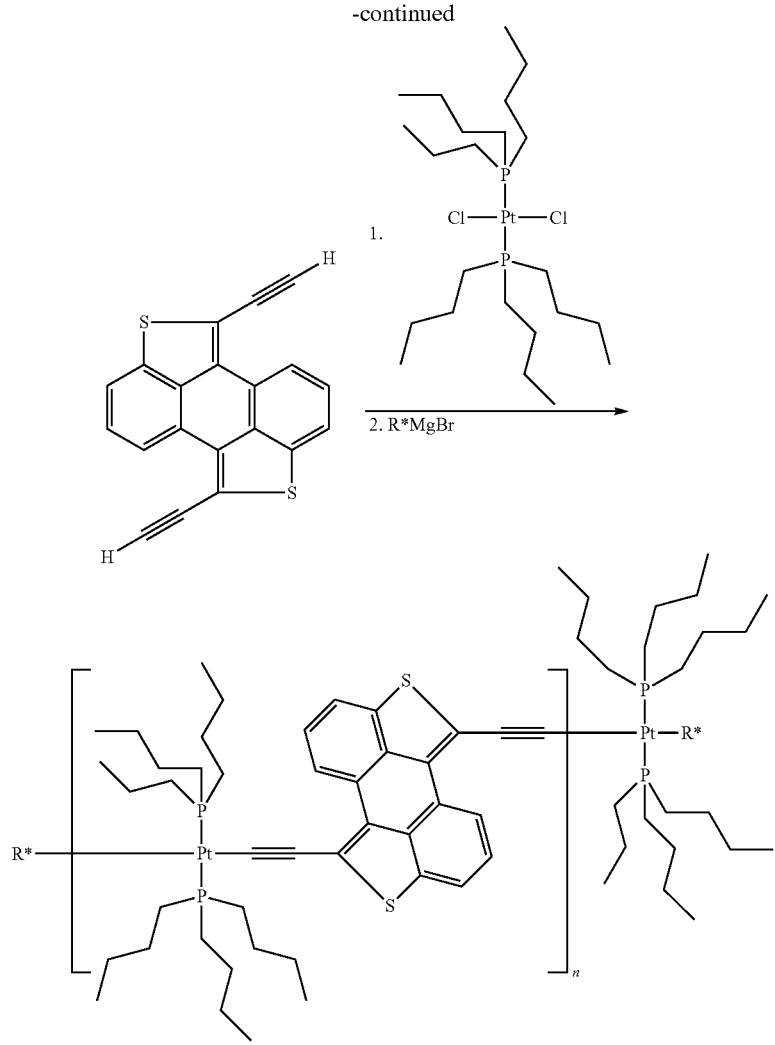
were R* is in each occurrence independently $C_4$-$C_{48}$ aryl, $C_4$-$C_{48}$ aryl containing a heteroatom of O, S, N, Se, or Te, $C_4$-$C_{48}$ fluoro aryl, $C_4$-$C_{48}$ fluoro aryl containing the heteroatom, $C_4$-$C_{48}$ perfluoro aryl, or $C_4$-$C_{48}$ perfluoro aryl containing the heteroatom.
Scheme 11:
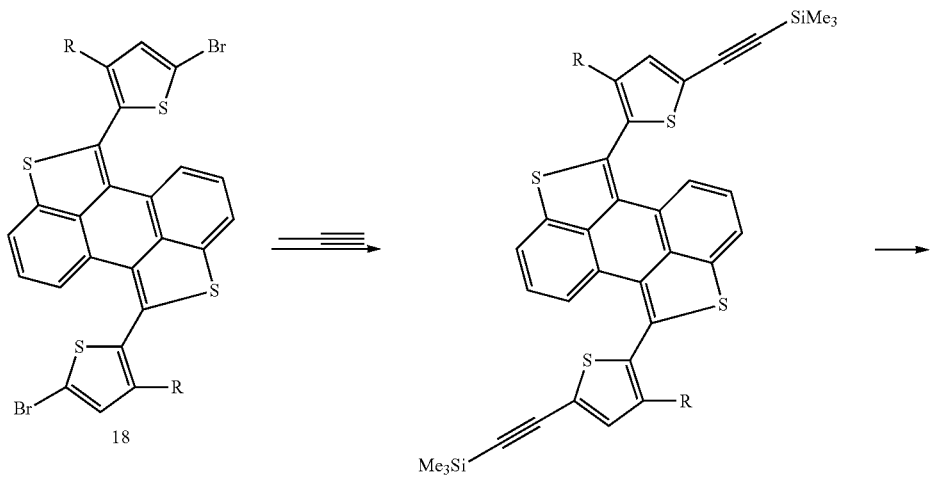

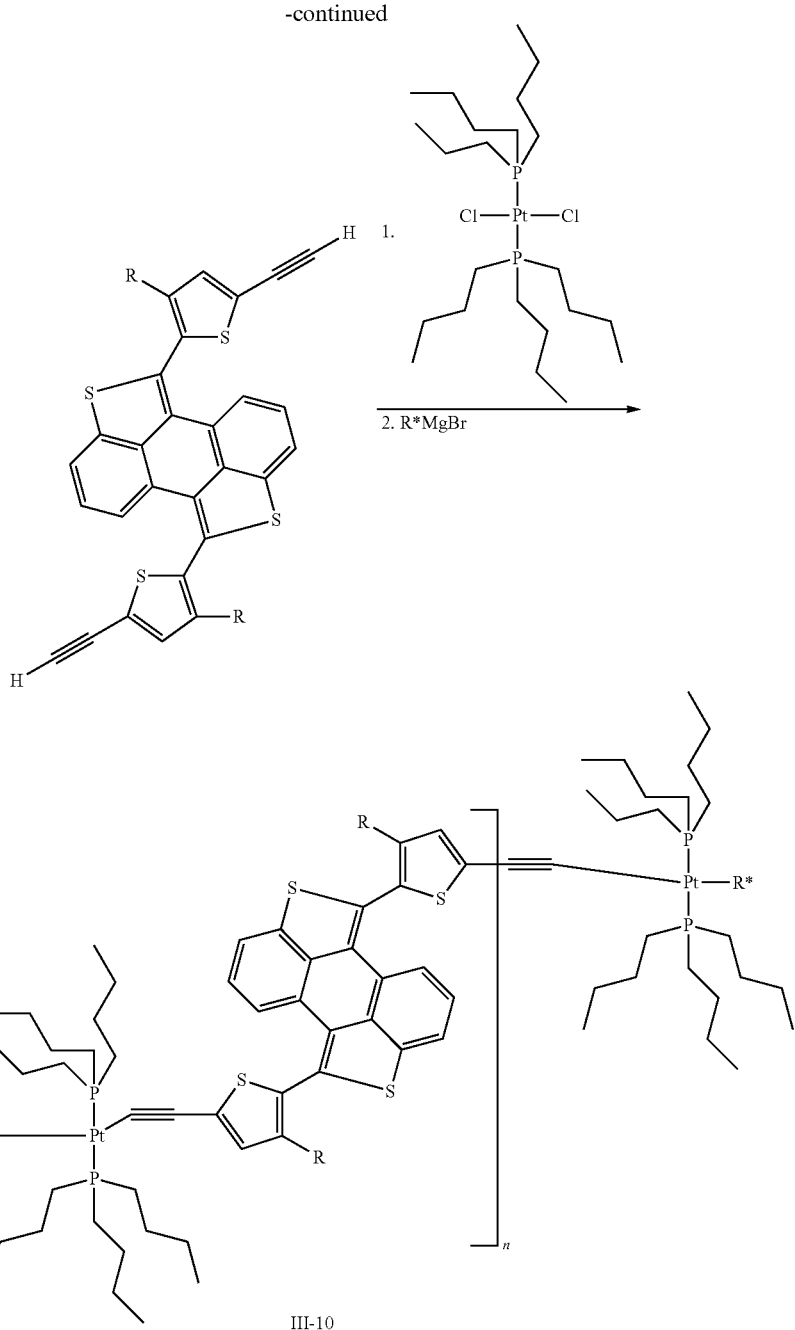
Scheme 12:
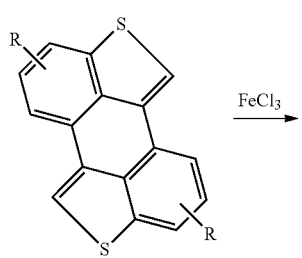
FeCl₃ →
-continued
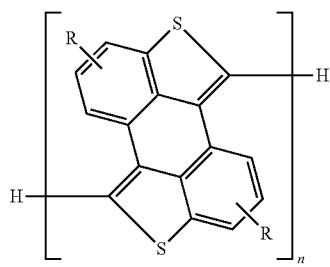

EXAMPLES

Having described the invention, the following examples are given to illustrate specific applications of the invention including the best mode now known to perform the invention. These specific examples are not intended to limit the scope of the invention described in this application.

The invention has been described in detail with particular reference to certain preferred embodiments thereof, but it will be understood that variations and modifications can be effected within the spirit and scope of the invention. The invention and its advantages are further illustrated by the specific examples as follows:

Example 1

Synthesis of Bis-2,2'-[(9,10-dihydro-9,10-dioxo-1,5-anthracenediyl)bis(thio)]acetic acid (2)

To a 3 liter three neck round flask equipped with water cooling condenser and mechanical stirring is added 150 g (0.54 mol.) of 1,5-dichloroanthraquinone, 2000 mL of dry ethanol and followed by slowly adding 100 mL (130 g, 1.41 mol) of thioglycolic acid, 8.0 g of MnO2 and 0.2 g of 18-crown-6 as a catalyst. The totally 320.0 g (1.79 mol) of potassium tert-butyloxide is slowly added to above mixture under nitrogen protection with the rate of to control the reaction temperature below 70 C with vigorously stirring. Then the reaction is continued for another four hours at around 70 C. After the reaction is cooled to room temperature, the reaction mixture is dissolved into 10 liter of water by pouring to 10 liter of water with mechanical stirring. Then result solution is filtered. The yellow precipitates are resulted by carefully adding 2.0 N of hydrochloric acid to the filtration. The yellow precipitates are filtered and washed with cool water and alcohol. After dried the crude Bis-2,2'-[(9,10-dihydro-9,10-dioxo-1,5-anthracenediyl)bis(thio)]acetic acid is used for next reaction without future purification.

Example 2

Synthesis of 3,4,3',4'-bibenzo[b]thiophene (3)

A suspension of 15.0 g of crude Bis-2,2'-[(9,10-dihydro-9,10-dioxo-1,5-anthracenediyl)-bis(thio)]acetic acid obtained from Example 1 (grounded as fine powder) in 500 mL of acetic anhydride is heated to reflux. The reaction is continued for two hours under refluxing after an evolving fine stream of gas has ceased. The reaction mixture is filtered hot, as the filtrate cooled, 5.5 g of black crystals separated. Yield is in 54.1% and a purity of 3,4,3',4'-bibenzo[b]thiophene is about 98%. The pure 3,4,3',4'-bibenzo[b]thiophene crystal is obtained by vacuum sublimation at 185 C.

Example 3

Synthesis of 2,7-dibromo-3,4,3',4'-bibenzo[b]thiophene (I-01)

To 350 of mL of dry DMF is added 5.6 g of pure 3,4,3',4'bibenzo[b]thiophene obtained from Example 2. The suspension is heated to about 140 C under nitrogen protection and until 3,4,3',4'-bibenzo[b]thiophene completely dissolved. Then the solution of 9.5 g of N-bromosuccinimide (NBS) in 60 mL of dry DMF is slowly added to above solution at about 60 C with vigorously stirring. 2,7-Dibromo-3,4,3',4'-bibenzo[b]thiophene precipitates were immediate formed. The reaction mixture is heated to keep at about 80 C for one hour with vigorously stirring. After cool, the precipitate is filtered and washed with acetone. A 8.6 pure 2,7-dibromo-3,4,3',4'-bibenzo[b]thiophene (I-01) is obtained in 100% of yield.

Example 5

Synthesis of 2,7-dicyano-3,4,3',4'-bibenzo[b]thiophene (I-02)

To suspension of 0.84 g of 2,7-dibromo-3,4,3',4'-bibenzo[b]thiophene obtained from Example 3 (grounded in fine powder) in 100 mL of dry DMF is added 1.5 g of copper (I) cyanide. The suspension is heated to 150 C with stirring under nitrogen protection for twelve hours. The reaction mixture is cooled and precipitates are filtered and washed with ethanol. A 0.5 g of pure 2,7-dicyano-3,4,3',4'-bibenzo[b]thiophene (I-02) is obtained by vacuum sublimation at 235 C. Yield 79.4%.

Examples 6-11

General Synthesis of Compounds I-04, I-05, I-06, I-10, I-11, and I-12

To reaction flask containing 1.0 mmol equivalent of 2,7-dibromo-3,4,3',4'-bibenzo[b]thiophene (I-01) are charged with 2.2 mmol equivalent of aryl boronic acid, 50 mg of 18-C-6 in a mixture of 70 mL of toluene, 30 mL of ethanol, and 25 mL of 2.0 N potassium carbonate. After mixture is bubbled with house nitrogen for 5 min, 0.1 g of Pd (PPh$_3$)$_4$ is added to the reaction mixture under nitrogen. Then the reaction mixture is heated to reflux with efficient stirring under nitrogen protection. After the reaction proceeded for three hours, 50 mg of Pd (PPh$_3$)$_4$ is added to the reaction mixture under nitrogen. The reaction mixture is continued to reflux for another two hours. The reaction mixture is cooled to room temperature and water phase is separated. The organic layer with the dissolved precipitates is washed with water three times (3×25 mL). The solvent is removed via vacuum rotary evaporator. 25 mL of alcohol is added to the residue and then the precipitates are filtered, washed with minimum amount of ethanol. The pure 2,7-diaryl substituted-3,4,3',4'-bibenzo[b]thiophene, compounds I-04, I-05, I-06, I-10, I-11, and I-12, are obtained after silica get chromatography purification (using mixture of toluene and dichloromethane as eluants).

| Examples | Compounds | Boronic Acids | Product Color |
|---|---|---|---|
| Example 6 | I-04 | | No color |
| Example 7 | I-05 | | Pale yellow |
| Example 8 | I-09 | | yellow |
| Example 9 | I-10 | | No color |
| Example 10 | I-11 | | No color |

| Examples | Compounds | Boronic Acids | Product Color |
|---|---|---|---|
| Example 11 | I-12 | 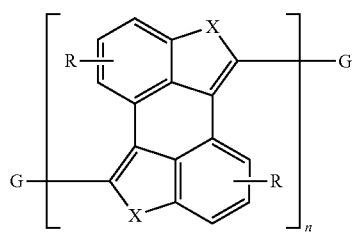 | Pale yellow |

Example 12

Synthesis of poly 2,7-[9,9-Bis-(2-ethyl-hexyl)-9H-fluoren-3-yl]-3,4,3',4'-bibenzo[b]thiophene (III-11)

To reaction flask containing 1.0 mmol equivalent of 2,7-dibromo-3,4,3',4'-bibenzo[b]thiophene (I-01) are charged with 2.0 mmol equivalent of 9,9-di(2'-ethylhexyl)fluorine-2,7-diboronic acid, 50 mg of 18-C-6 in a mixture of 70 mL of toluene and 25 mL of 2.0 N potassium carbonate. After mixture is bubbled with house nitrogen for 5 min, 0.1 g of Pd (PPh$_3$)$_4$ is added to the reaction mixture under nitrogen. Then the reaction mixture is heated to reflux with efficient stirring under nitrogen protection. After the reaction proceeded for three hours, 50 mg of Pd (PPh$_3$)$_4$ is added to the reaction mixture under nitrogen. After reaction mixture is continued to reflux for overnight, three drop of bromobenzene is added to reaction mixture through the syringe. The reaction mixture is continued to reflux for another one hour. Then the reaction mixture is cooled to room temperature and water phase is separated. The organic layer with the dissolved precipitates is washed with water three times (3×25 mL). The solvent is removed via vacuum rotary evaporator. 25 mL of alcohol is added to the residue and then the precipitates are filtered, washed with minimum amount of ethanol. Then the precipitates are dissolved in tetrahydrofuran (THE) and precipitate from ethanol. The pure 2,7-[9,9-Bis-(2-ethyl-hexyl)-9H-fluoren-3-yl]-3,4,3',4'-bibenzo[b]thiophene (III-11) is obtained after repeat this process. The poly 2,7-[9,9-Bis-(2-ethyl-hexyl)-9H-fluoren-3-yl]-3,4,3',4'-bibenzo[b]thiophene is deep yellow color.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof are intended to define the scope of the invention.

The invention claimed is:

1. A compound having the formula:

I where
X is S, Se or Te;
R is in each occurrence independently H, $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, $C_4$-$C_{48}$ aryl containing a heteroatom, the heteroatom being O, N, S, Se or Te, $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom;
G in each occurrence is independently fluorine, chlorine, bromine, iodine, cyano, isocyano, R, with the proviso that R is not H, Q, E or

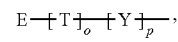

E is R or Q with the proviso R is not H;
T is independently in each occurrence of each of T is -M-(P—R$_3^1$)$_q$(R)$_{3-q}$, or R-Q with the proviso that R is not H;
Y is independently in each occurrence of each of Y is -M-(P—R$_3^1$)$_q$(R)$_{3-q}$, or R-Q with the proviso that R is not H;

Q is a polymerizing functional group of

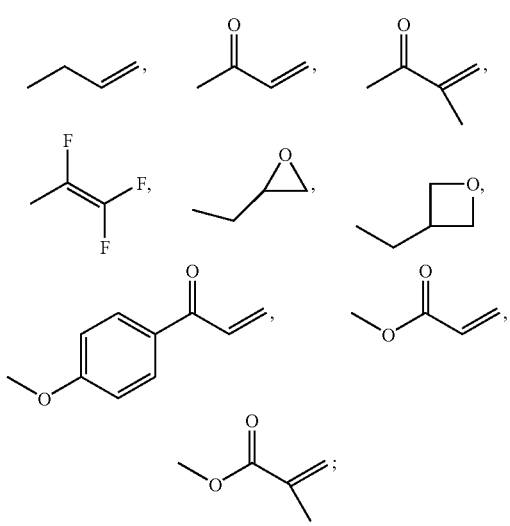

o is an integer from 0 to 100 inclusive;
p is an integer from 0 to 100 inclusive;
M is a transition metal of Pt, Ni or Pd;
$R^1$ is independently in each occurrence $C_1$-$C_{12}$ alkyl;
q is an integer from 0 to 3 inclusive; and
n is an integer from 1 to 250 inclusive.

2. The compound of claim 1, wherein R in each occurrence $C_1$-$C_{48}$ alkyl, $C_6$-$C_8$ cycloalkyl, $C_2$-$C_{48}$ alkenyl, $C_6$-$C_8$ cycloalkenyl, $C_2$-$C_{48}$ alkynyl, $C_4$-$C_{48}$ aryl, or $C_4$-$C_{48}$ aryl containing the heteroatom.

3. The compound of claim 1, wherein R is in each occurrence $C_1$-$C_{48}$ fluoro alkyl, $C_6$-$C_8$ fluoro cycloalkyl, $C_2$-$C_{48}$ fluoro alkenyl, $C_6$-$C_8$ fluoro cycloalkenyl, $C_2$-$C_{48}$ fluoro alkynyl, $C_4$-$C_{48}$ fluoro aryl, $C_4$-$C_{48}$ fluoro aryl containing the heteroatom; $C_1$-$C_{48}$ perfluoro alkyl, $C_6$-$C_8$ perfluoro cycloalkyl, $C_2$-$C_{48}$ perfluoro alkenyl, $C_6$-$C_8$ cycloperfluoro alkenyl, $C_2$-$C_{48}$ perfluoro alkynyl, $C_4$-$C_{48}$ perfluoro aryl, or $C_4$-$C_{48}$ perfluoro aryl containing the heteroatom.

4. The compound of claim 1, wherein R is in at least one occurrence the $C_4$-$C_{48}$ heteroatom containing aryl of:

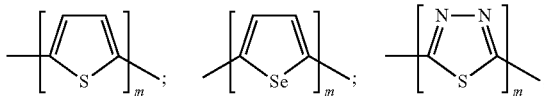

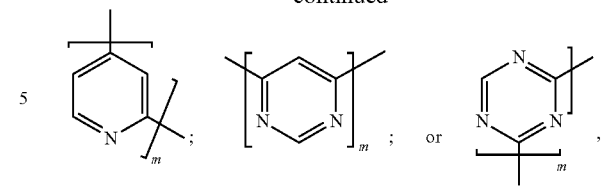

where m is an integer of between 1 and 12 inclusive.

5. The compound of claim 1, wherein G is in every occurrence the same and one of fluorine, chlorine or bromine.

6. The compound of claim 5, wherein G is in every occurrence

7. The compound of claim 6, wherein there is only a single Q per

8. The compound of claim 1, wherein n is 1 and R and G are such that the compound is:

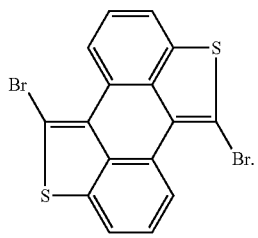

9. The compound of claim 1, wherein said compound is:

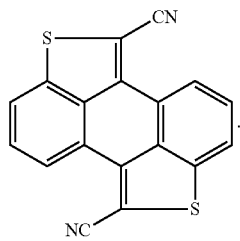

10. The compound of claim 1, wherein R and G are such that the compound is:

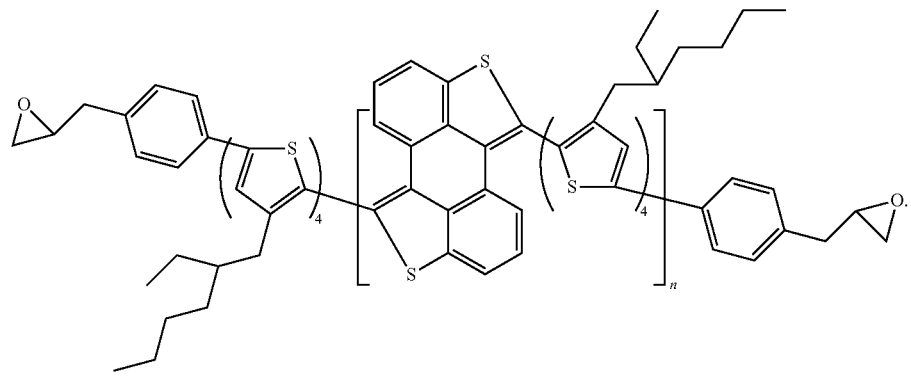

11. The compound of claim 1, wherein R and G are such that the compound is:
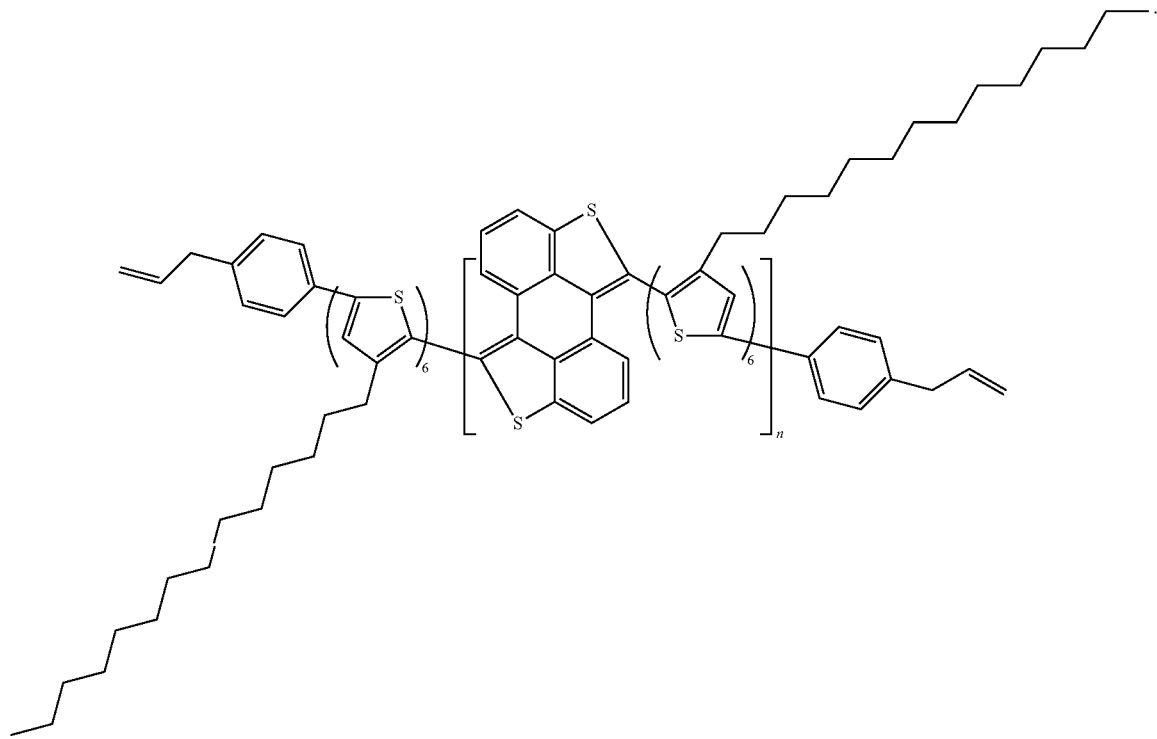
12. The compound of claim 1, wherein R and G are such that the compound is:
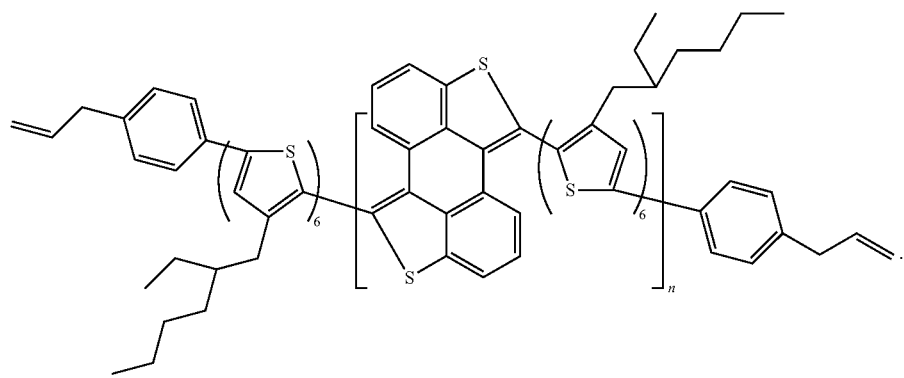

13. The compound of claim 1, wherein R and G are such that the compound is:
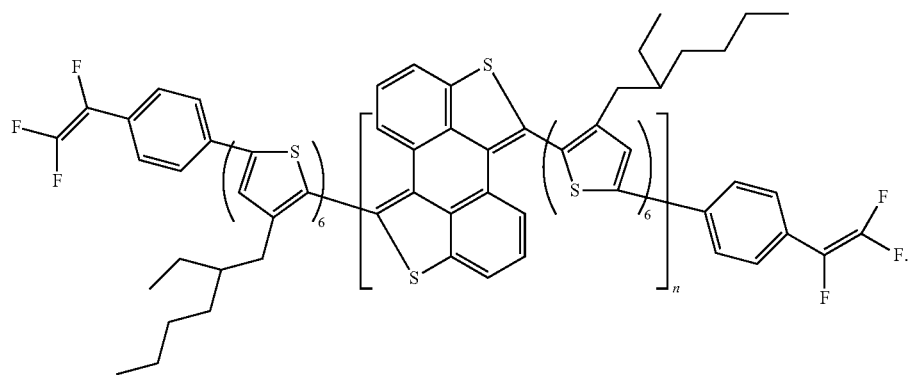
14. The compound of claim 1, wherein R and G are such that the compound is:
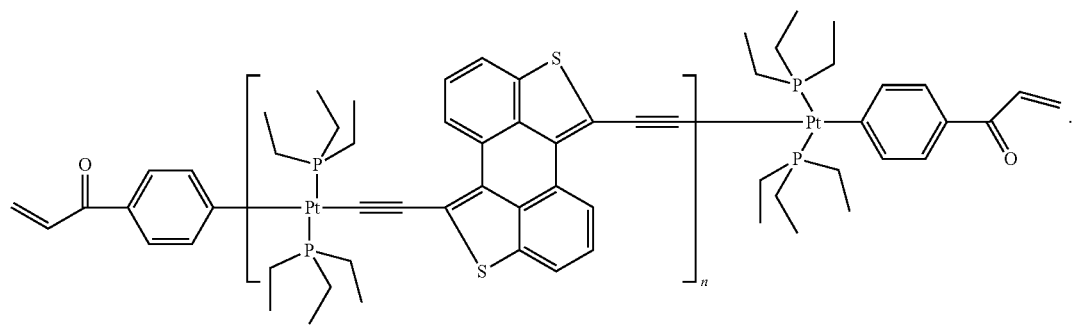
15. The compound of claim 1, wherein R and G are such that the compound is:
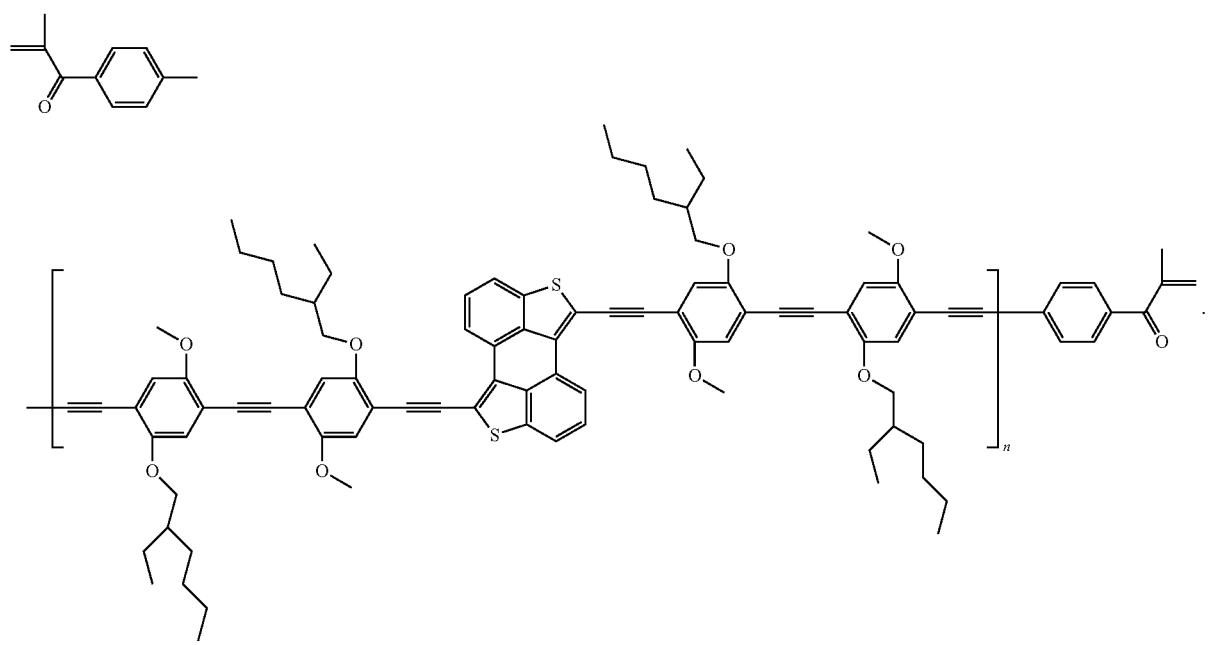

16. The compound of claim 1, wherein R and G are such that the compound is:
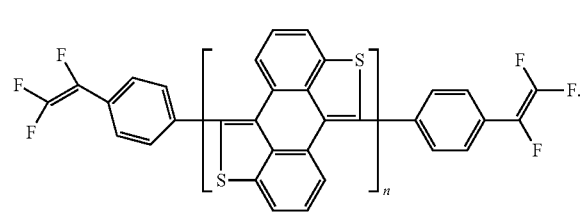
17. The compound of claim 1, wherein R and G are such that the compound is:
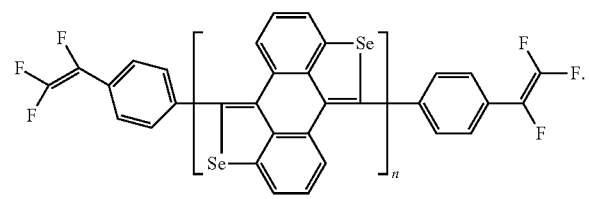
* * * * *